United States Patent
Chung et al.

(10) Patent No.: US 8,641,970 B2
(45) Date of Patent: Feb. 4, 2014

(54) MOBILE ROBOT AND CLINICAL TEST APPARATUS USING THE SAME

(75) Inventors: Wan Kyun Chung, Gyeongsangbuk-do (KR); Hyouk Ryeol Choi, Gyeonggi-do (KR); Sung Moo Ryu, Gyeonggi-do (KR); Min Chul Kim, Gyeonggi-do (KR); Ja Choon Koo, Gyeonggi-do (KR)

(73) Assignee: Postech Academy-Industry Foundation, Gyeongsangbuk-do (KR)

( * ) Notice: Subject to any disclaimer, the term of this patent is extended or adjusted under 35 U.S.C. 154(b) by 1054 days.

(21) Appl. No.: 12/162,131

(22) PCT Filed: Jul. 13, 2007

(86) PCT No.: PCT/KR2007/003406
§ 371 (c)(1),
(2), (4) Date: Jul. 25, 2008

(87) PCT Pub. No.: WO2008/007923
PCT Pub. Date: Jan. 17, 2008

(65) Prior Publication Data
US 2009/0035181 A1  Feb. 5, 2009

(30) Foreign Application Priority Data
Jul. 13, 2006 (KR) .................. 10-2006-0065662

(51) Int. Cl.
*B32B 5/02* (2006.01)
*G01N 15/06* (2006.01)
*G01N 1/10* (2006.01)

(52) U.S. Cl.
USPC .................. 422/67; 422/63; 422/64; 422/65; 422/66

(58) Field of Classification Search
USPC ........................ 422/63–67, 99, 100
See application file for complete search history.

(56) References Cited

U.S. PATENT DOCUMENTS

| | | | |
|---|---|---|---|
| 6,534,014 B1 * | 3/2003 | Mainquist et al. | 422/99 |
| 7,674,581 B1 * | 3/2010 | Fries et al. | 435/6 |
| 7,729,801 B2 * | 6/2010 | Abramson | 700/245 |
| 2002/0146347 A1 * | 10/2002 | McNeil | 422/63 |
| 2004/0191923 A1 | 9/2004 | Tomasso et al. | |
| 2004/0193339 A1 * | 9/2004 | Hulden | 701/23 |
| 2005/0064535 A1 | 3/2005 | Favuzzi et al. | |
| 2006/0261772 A1 * | 11/2006 | Kim | 318/587 |

FOREIGN PATENT DOCUMENTS

JP   04-134262   5/1992

* cited by examiner

Primary Examiner — Sally Merkling
(74) Attorney, Agent, or Firm — Occhiuti & Rohlicek LLP

(57) ABSTRACT

A clinical test apparatus employing a mobile robot is provided. The clinical test apparatus includes a stage unit, a test station provided in the stage unit and configured to perform a clinical test, a mobile robot configured to move on a top surface of the stage unit and to transfer a plate on which samples and reagents are loaded to the test station, and a docking unit disposed in the stage unit and configured to reset a position of the mobile robot. A variety of test stations for a clinical test can be integrated, and multiple tests can be performed at the same time through a plurality of mobile robots.

10 Claims, 4 Drawing Sheets

MOBILE ROBOT AND CLINICAL TEST APPARATUS USING THE SAME

CROSS-REFERENCE TO RELATED APPLICATIONS

This application is the National Stage of International Application No. PCT/KR2007/003406, filed on Jul. 13, 2007, which claims the priority of Korean Application No. 10-2006-0065662, filed on Jul 13, 2006. The contents of both applications are hereby incorporated by reference in their entirety.

TECHNICAL FIELD

The present invention relates to an apparatus for performing clinical tests, and more particularly, to a clinical test apparatus employing a mobile robot.

BACKGROUND ART

Since human beings appear on the earth, human beings have attempted various means and methods for realizing the dream of longer life in order to live long without being attacked by diseases. In recent years, new techniques capable of preventing various diseases and extending life by leaps and bounds have been developed. As the living of human beings become wealthy, an interest in a human being himself/herself and his/her family has been increasing.

A time has changed from an era where a patient goes to a hospital in order to cure his/her diseases to an era where a man goes to a hospital in order to prevent diseases and have his healthy status tested and managed. In order to confirm a personal healthy status, various kinds of clinical tests have been carried out.

A clinical test includes a hematological test, immunoassay, toxicology, and a test of other specific categories for testing samples of biological materials, such as urinalysis, blood, serum and urine. The clinical test provides invaluable information related to a person's healthy status. The results of the clinical test are generally used for diagnostic evaluation, surgical decision-making, and recognition of variation occurring in a patient's healthy status.

The clinical test includes an esoteric costly process of generating information with high accuracy. In order to save the expenses spent for the clinical test, an automated apparatus has emerged.

U.S. Pat. No. 6,374,989 entitled "Conveyor System for Clinical Test Apparatus" discloses a conveyer system for a clinical test equipped with an auxiliary conveyor lane. U.S. Pat. No. 5,623,415 entitled "Automated Sampling and Testing of Biological Materials" discloses an automated apparatus in which a transport lane and a queue lane are disposed and a sample is transferred from the queue lane to the transport lane.

A conveyer or other means for transporting samples or reagents are generally bulky, and specialized in a particular clinical test apparatus. They have the characteristics of permanence and inflexibility, once being mounted in a system. For example, if abnormality occurs in the conveyer, the whole system has to be stopped.

In order to save the expenses spent for the clinical test, the test needs to be made as fast as possible. In accordance with the conventional conveyer system, one conveyer can transfer only one sample or reagent at a time. Thus, the conventional conveyer system has a serial structure in which one clinical test is performed at a time.

In order to realize a custom-made clinical test in conformance with the forthcoming clinical test trend, there is a need for a clinical test apparatus having flexibility and miniaturization.

DISCLOSURE OF INVENTION

Technical Problem

An object of the present invention is to provide a clinical test apparatus capable of performing a plurality of clinical tests in parallel.

Another object of the present invention is to provide a mobile robot that provides flexibility to a clinical test apparatus.

Technical Solution

In one aspect, a clinical test apparatus includes a stage unit, a test station provided in the stage unit and configured to perform a clinical test, a mobile robot configured to move on a top surface of the stage unit and to transfer a plate on which samples and reagents are loaded to the test station and a docking unit disposed in the stage unit and configured to reset a position of the mobile robot.

In another aspect, a mobile robot includes a diagnostic module in which a plate having samples and reagents loaded thereon is seated, and a mobile module having the diagnostic module mounted therein and configured to transfer the diagnostic module to a test station where a clinical test is performed.

Advantageous Effects

A variety of test stations for a clinical test can be integrated, and multiple tests can be performed at the same time through a plurality of mobile robots. It is therefore possible to reduce the time taken for a clinical test. Further, installation flexibility can be provided to a clinical test apparatus through a small-sized mobile robot, and the volume of an overall apparatus can be reduced.

MODE FOR THE INVENTION

Figure 1:
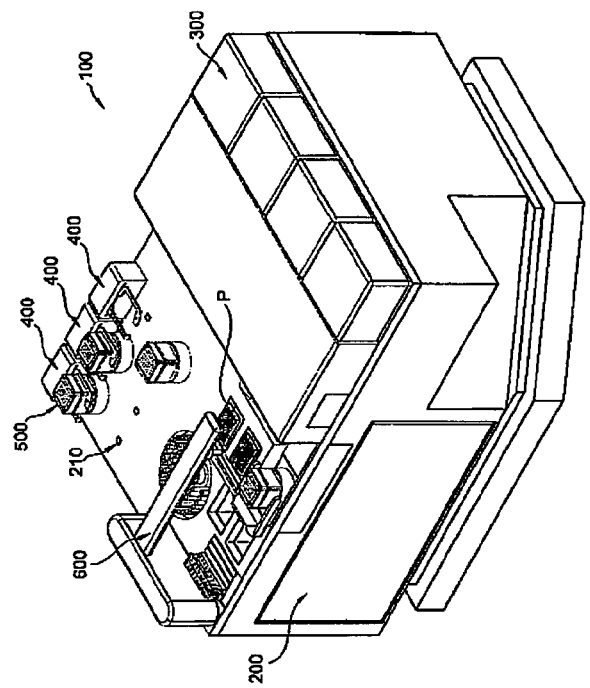
FIG. 1 is a perspective view illustrating a clinical test apparatus.

FIG. 1 is a perspective view illustrating a clinical test apparatus.

Referring to FIG. 1, a clinical test apparatus 100 includes a stage unit 200, a test station 300, a docking unit 400, a mobile robot 500 and a transfer unit 600.

The stage unit 200 forms an overall frame, and has a test station 300, a docking unit 400 and a transfer unit 600 mounted on its top surface. An incubator (not shown) is disposed within the stage unit 200 under the test station 300. The mobile robot 500 travels on a top surface of the stage unit 200, and moves a plate P, mounted on the mobile robot 500, to the test station 300, the docking unit 400 and the transfer unit 600. On the top surface of the stage unit 200 is disposed a plurality of landmarks 210. The landmarks 210 represents reference position to adjust positional error of the mobile robot 500.

The test station 300 is an apparatus for performing an clinical test, and extracts clinical test results through a reaction of a reagent and a sample loaded on the transferred plate P. As will be described later on, the test station 300 is equipped with a light source (not shown). The light source radiates light on the plate P on which the reagent and the sample are loaded. The test station 300 calculates clinical test results by measuring the transmittance of light from a detector (525 in FIG. 2) included in the diagnostic module of the mobile robot 500.

The docking unit 400 is a place at which the mobile robot 500 takes an initialization position. The mobile robot 500 docks at the docking unit 400 and resets its positional information. Further, if the mobile robot 500 docks at the docking unit 400, a battery (not shown) built in the mobile robot 500 can be charged.

The transfer unit 600 loads/unloads the plate P on/from the mobile robot 500, and also puts a sample and/or a reagent to the plate P.

Figure 2:
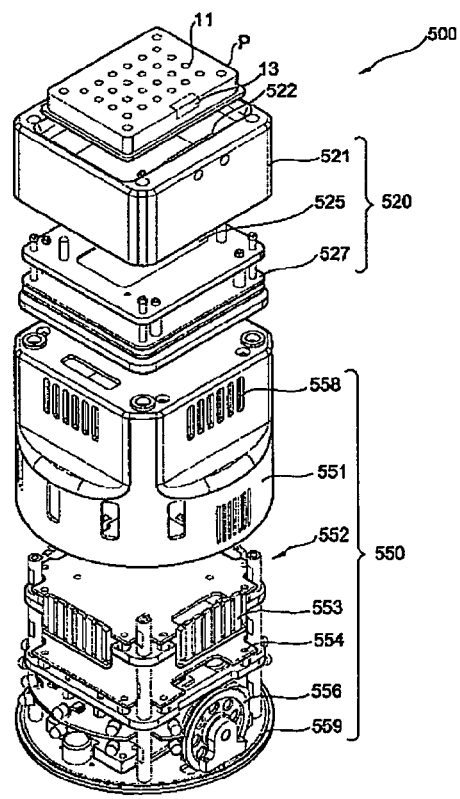
FIG. 2 is a dismantled perspective view illustrating a mobile robot.

FIG. 2 is a dismantled perspective view illustrating a mobile robot.

Referring to FIG. 2, the mobile robot 500 includes a diagnostic module 520 and a mobile module 550. The mobile module 550 has the diagnostic module 520 mounted on its top surface, and moves over the top surface of the stage unit 200. The diagnostic module 520 has the plate P mounted thereon, and it recognizes clinical test information from the plate P and calculates clinical test results while operating in conjunction with the test station 300.

The plate P is a medical plate in which a plurality of grooves 11 are arranged at regular intervals and a sample is placed in the groove 11. Thus, a clinical test can be performed by putting a reagent on the plate. The plate P can be formed of a transparent material. A Radio Frequency IDdentification (RFID) tag 13, including clinical test information about a sample, a reagent, etc., which are loaded on the plate P, is attached to the plate P. The RFID tag 13 is only illustrative. Alternatively, a barcode including clinical test information can be attached to the plate P.

The diagnostic module 520 includes a diagnostic cover 521, a RFID reader 522, a detector 525 and an interface board 527.

The diagnostic cover 521 forms an body of the diagnostic module 520, and has the plate P seated in its top.

The RFID reader 522 is disposed in the diagnostic cover 521, and reads the RFID tag 13 attached to the plate P seated in the diagnostic cover 521. The RFID tag 13 includes clinical test information, such as patient information. The clinical test information read from the RFID tag 13 is transferred to a DSP (Digital Signal Processor) (not shown) of an electric board 554 of the mobile module 550 through the interface board 527. The clinical test information is then sent to the test station 300.

The detector 525 is fixed to the diagnostic cover 521, and is disposed opposite to a rear surface of the plate P. The detector 525 measures clinical test results when the plate P enters the test station 300 in order to perform a clinical test. The detector 525 may be a spectrophotometer. If a light source of the test station 300 emits light over the plate P, the transmittance of light that passes through a place where the sample and the reagent react to each other is changed. The detector 525 disposed at the rear of the plate P reads the light whose transmittance has been changed, and transmits it to the test station 300, so that clinical test results can be known.

The interface board 527 includes a microprocessor, and it is connected to the electric board 554 of the mobile module 550 and communicates with the DSP disposed in the electric board 554.

The mobile module 550 includes an external body 551 to form an outer appearance, and an internal body 552 disposed within the external body 552. The internal body 552 includes a charging connector 553, the electric board 554, a wheel 556 and a base 559. The charging connector 553 is connected to a charging terminal of the docking unit 400 to be described later on, and serves to charge the battery (not shown) mounted in the internal body 552. The battery may be a lithium-ion battery. Grooves 558 are formed in the external body 551 corresponding to the charging connector 553, thus causing the charging connector 553 to be exposed to the outside. The electric board 554 has the DSP (not shown), serving as a controller of the mobile robot 500, and a Bluetooth module (not shown) mounted therein. The base 559 is disposed at the bottom of the internal body 556. A pair of the wheels 556 is disposed in the base 559, and provides driving force of the mobile robot 500. To the wheels 556 are coupled a motor (not shown), which provides the wheels with driving power, and also coupled an encoder (not shown), which measures the position of the mobile robot 500.

Ultrasonic sensors (not shown) are mounted around the mobile module 550, and sense collision between the mobile robots 500, which may occur when a plurality of the mobile robots 500 are operated.

Figure 3:
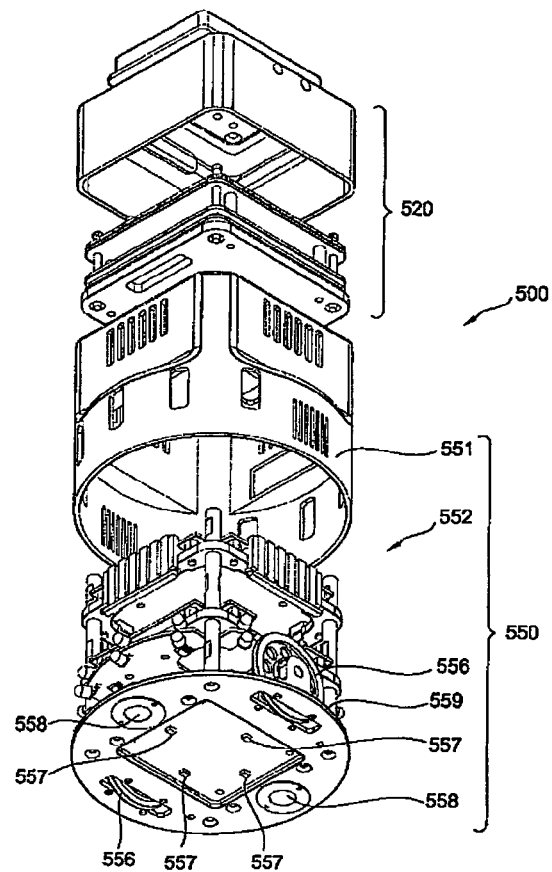
FIG. 3 is a perspective view illustrating a bottom surface of the mobile robot.

FIG. 3 is a perspective view illustrating a bottom surface of the mobile robot.

Referring to FIG. 3, two wheels 556 are projected externally from the base 559 of the mobile module 550. The wheels 556 are brought in contact with the top surface of the stage unit 200, so that the mobile robot 500 can move on the top surface of the stage unit 200 by frictional force. Two ball casters 558 are disposed in the base 559 in a longitudinal direction (this is referred to as a front and rear direction of the mobile robot 500), which is substantially vertical to a lateral direction (this is referred to as a left and right direction of the mobile robot 500) where the two wheels 556 form. When the mobile robot 500 is moved, two ball casters 558 can be prevented from being inclined in front and in the rear.

Four hall sensors 557 are disposed at the bottom of the base 559 of the mobile module 550. The hall sensors 557 are disposed in a square shape, and correct the position of the mobile robot 500 by using the hall effect.

Figure 4:
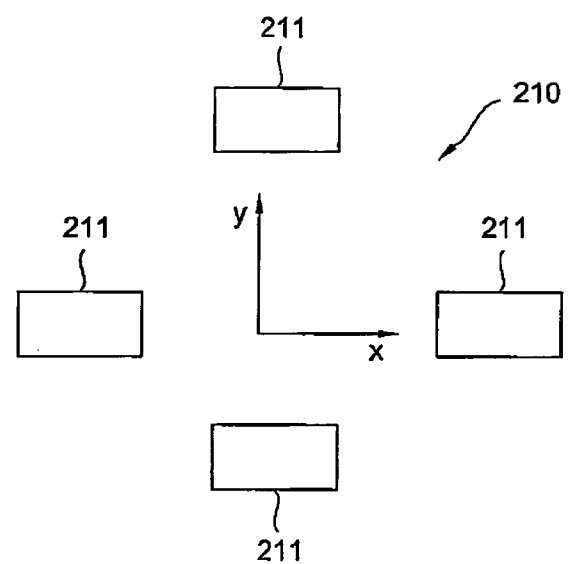
FIG. 4 illustrates landmarks disposed in a stage unit.

FIG. 4 illustrates landmarks disposed in a stage unit.

Referring to FIG. 4, the landmark 210 is disposed in plural numbers on the top surface of the stage unit 200, and includes four permanent magnets 211. It can be said that the landmark 210 is an absolute coordinate of the stage unit 200.

The mobile robot 500 has traveling error due to several causes when traveling on the stage unit 200. The causes of traveling error include wheel fabrication tolerance, a difference in a point of contact between both wheels, sliding error when the mobile robot 500 contacts the top surface of the stage unit 200, environmental factors such as irregularity of the surface, resolution of an encoder.

As the mobile robot 500 moves from an original position to a target position, positional error is accumulated. The mobile robot 500 may reach a different position not a target position due to such positional error. In order to perform a clinical test, scheduling is necessary based on accurate positional information of the mobile robot 500, and therefore positional error needs to be corrected.

The hall sensors 557 attached to the bottom surface of the mobile robot 500 recognize magnetic fields of the landmarks 210. When the mobile robot 500 passes through the landmarks 210, the hall sensors 557 recognize the permanent magnets 211, and measure an offset between coordinates of the magnetic field and coordinates of the mobile robot 500.

The hall effect refers to the potential difference on the surface of a conductor or semiconductor on which electrons or holes are moved when applying a DC voltage to the conductor or semiconductor in a magnetic field. However, in detecting the magnetic fields of the permanent magnets by the hall sensors, a characteristic thereof is not linear. Thus, in order to detect the distance, sensor correction is indispensable. Hall sensor correction is not required with respect to a distance vertical to the magnets since the distance between the hall sensor and the permanent magnet is not fixed. If correction is to be performed with respect to a horizontal position, it can be assumed that a voltage according to the distance is output linearly.

Figure 5:
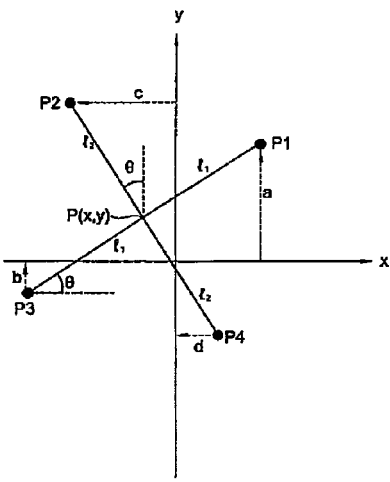
FIG. 5 shows coordinates illustrating a positioning algorithm.

FIG. 5 shows coordinates illustrating a positioning algorithm.

Referring to FIG. 5, x-y coordinates are coordinates with respect to the four permanent magnets 211 of the landmark 210. Four points P1, P2, P3, and P4 refer to the positions of the four hall sensors 577 attached to the mobile robot 500. Assuming that a center point coordinate of the mobile robot 500 is P, coordinates (x,y) of the center point P from the original point of the x-y coordinates and a slope θ are found.

Assuming that a distance of each point P1, P2, P3 and P4 from the center point P is $l_1$, $l_2$, an offset with an x axis of the point P1 is 'a', an offset with an y axis of the point P2 is 'b', an offset with the x axis of the point P3 is 'c', and an offset with the y axis of the point P4 is 'd', the coordinates (x,y) of the center point P and the slope θ can be expressed in the following equation.

$$x = l_1 \sin\theta + b \quad \text{MathFigure 1}$$
$$= l_1 \times \left(\frac{a-b}{2l_1}\right) + b$$
$$= \frac{a-b}{2} + b$$

$$y = l_2 \sin\theta + d \quad \text{MathFigure 2}$$
$$= l_2 \times \left(\frac{c-d}{2l_2}\right) + d$$
$$= \frac{c-d}{2} + d$$

$$\theta = \arcsin\left(\frac{|a-b|}{2l_1}\right), \quad \text{MathFigure 3}$$
if $a - b > 0$ then $\theta > 0$, else if $a - b < 0$ then $\theta < 0$
or
$$\theta = \arcsin\left(\frac{|c-d|}{2l_2}\right),$$
if $c - d > 0$ then $\theta > 0$, else if $c - d < 0$ then $\theta < 0$ where a, b, c and d refer to a difference of the coordinates between the permanent magnets and the mobile robot 500. (x, y) refer to a distance between a target arrival position and an error position. θ refers to a difference in the angle between a target arrival reference coordinate and an actual coordinate of the mobile robot 500. Thus, when the mobile robot 500 reaches a target point, an error value between an actual position and an arrival position can be measured, and coordinates of a next movement target position can be corrected.

The hall sensors have been used in order to detect the position of the mobile robot 500, but the technical spirit of the present invention is not limited thereto. As an embodiment, magnetic lines may be installed in the stage unit 200 along the path of the mobile robot 500, and the position of the mobile robot 500 may be corrected while the mobile robot 500 moves along the magnetic lines. As an alternative embodiment, a camera may be installed over the stage unit 200, and the position of the mobile robot 500 may be tracked in real-time through the camera.

Meanwhile, it is necessary not only to reset an absolute position of the mobile robot 500, but also to initialize the position of the mobile robot 500 on the stage unit 200. Further, a battery is built in the mobile robot 500 for miniaturization, and charging of the battery is also needed.

Figure 6:
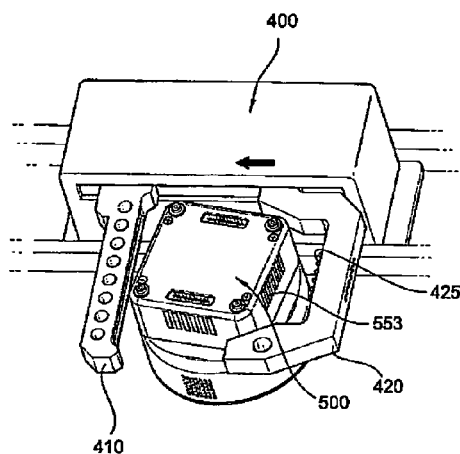
FIG. 6 shows an example in which the mobile robot enters a docking unit.

FIG. 6 shows an example in which the mobile robot enters the docking unit.

Referring to FIG. 6, the docking unit 400 includes a fixed reference gripper 410, and a movement gripper 420 that moves horizontally. The reference gripper 410 is fixed to the stage unit 200, and it contacts at least one surface of the mobile robot 500 and takes a reference position. The movement gripper 420 contacts at least one surface of the mobile robot 500. As the movement gripper 420 moves, the mobile robot 500 slides and is then inserted between the movement gripper 420 and the reference gripper 410.

In order to move the movement gripper 420, a well-known driving mechanism may be used. For example, a pneumatic actuator, a linear motor, a belt & pully structure, a ball screw and so on may be used.

Charging terminals 425 are disposed on an inner surface (a surface to contact one surface of the mobile robot 500) of the movement gripper 420. As the movement gripper 420 is brought in contact with the mobile robot 500, the charging terminals 425 contact the charging connectors 553 of the mobile robot 500, and charge the battery of the mobile robot 500. The docking unit 400 not only resets the position of the mobile robot 500, but also performs a charging function. Although the charging terminals 425 are mounted in the movement gripper 420, they may be mounted in the reference gripper 410, or may be mounted both in the movement gripper 420 and the reference gripper 410.

Initially, the reference gripper 410 and the movement gripper 420 are spaced apart from each other. The mobile robot 500 approaches the docking unit 400, and enters between the reference gripper 410 and the movement gripper 420. As the movement gripper 420 moves toward the reference gripper 410, the mobile robot 500 contacts the movement gripper 420, and thus moves. As the movement gripper 420 and the mobile robot 500 are brought in contact with each other, the charging terminal 425 and the charging connector 553 are also brought in contact with each other.

Figure 7:
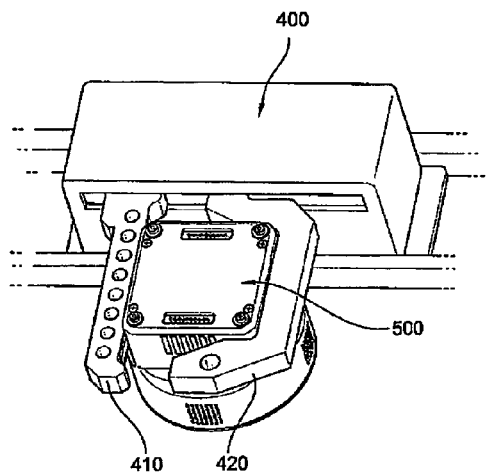
FIG. 7 shows the mobile robot docked at the docking unit.

FIG. 7 shows the mobile robot docked at the docking unit.

Referring to FIG. 7, the mobile robot 500 is inserted between the reference gripper 410 and the movement gripper 420 of the docking unit 400, and the docking unit 400 is coupled to the mobile robot 500 at a set position. If the mobile robot 500 is grapped by the reference gripper 410 and the movement gripper 420, the position of the mobile robot 500 is reset, which becomes a reference position. If the docking unit 400 is connected to the mobile robot 500, the battery of the mobile robot 500 is charged through the charging terminals 425.

The reference position of the mobile robot 500 can also be set by the docking unit 400. By commanding the mobile robot 500 to pass through the docking unit 400 periodically or non-periodically, positional error can be minimized.

Figure 8:
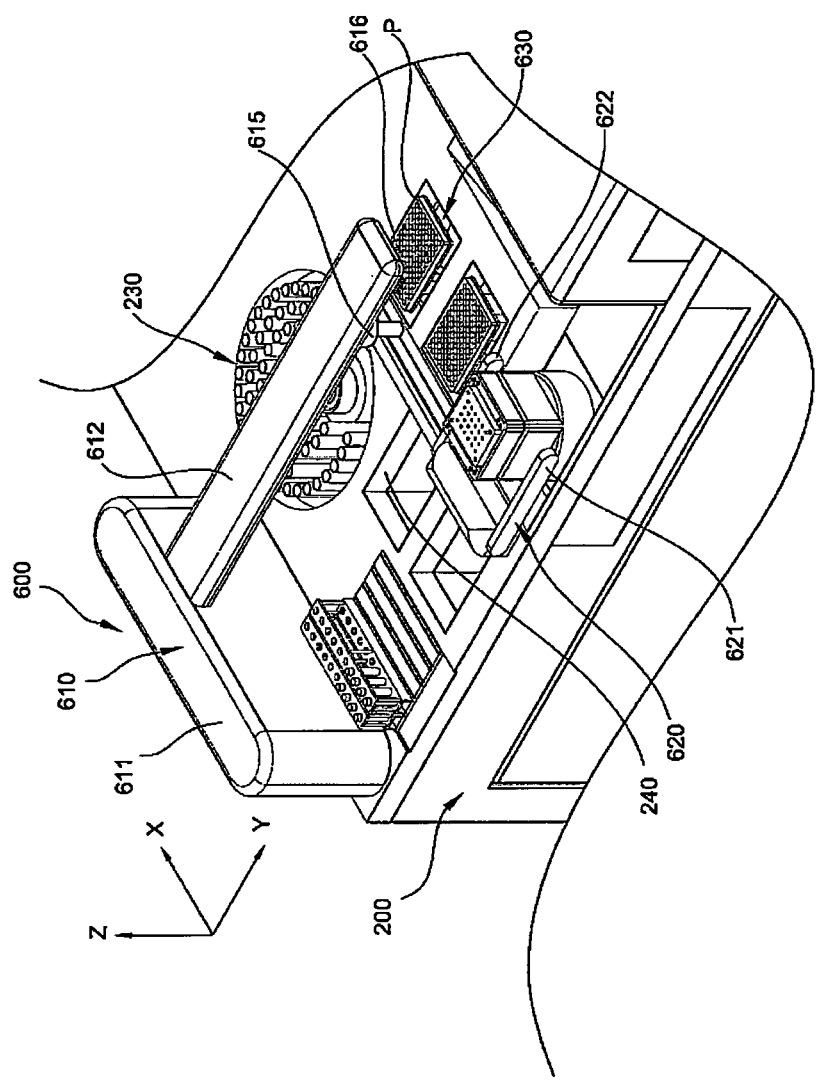
FIG. 8 is an exaggerated perspective view of a transfer unit shown in FIG. 1.

FIG. 8 is an exaggerated perspective view of the transfer unit shown in FIG. 1.

Referring to FIG. 8, the transfer unit 600 includes a transfer robot 610, a reference robot 620 and a plate lift unit 630.

The transfer robot 610 can move horizontally (X-Y) and vertically (Z), and is used to carry the plate P and the sample/reagent. The transfer robot 610 includes a XZ driving unit 611, an arm 612 coupled to the XZ driving unit 611 and configured to inwardly extend, a plate transfer unit 615 disposed at one side of the arm 612, and a sample/reagent transfer unit 616. The XZ driving unit 611 can move in the X- and Z-axis directions (vertically). The arm 612 is coupled to the XZ driving unit 611, and expands or contracts in the Y-axis direction.

The plate transfer unit 615 and the sample/reagent transfer unit 616 are mounted on one side of the arm 612. The plate transfer unit 615 seats the plate P, supplied from the plate lift unit 630, in the mobile robot 500, or discharges the plate P, seated in the mobile robot 500, to an exhaust port 240. The exhaust port 240 is a hole provided at the top of the stage unit 200. The plate P on which a clinical test has been completed is processed in the exhaust port 240. The sample/reagent transfer unit 616 extracts samples/reagents from a plurality of test tubes loaded on a loading unit 230, and distributes them into the plates P. The loading unit 230 is disposed on a top surface of the stage unit 200 and has the plurality of the test tubes disposed thereon. Samples or reagents are loaded on the plurality of test tubes.

The reference robot 620 fixes the mobile robot 500, so that the transfer robot 610 safely seats the plate P in the mobile robot 500. The reference robot 620 includes two fingers 621, 622. The mobile robot 500 enters between the two fingers 621, 622, and at least one of the fingers moves and fixes the mobile robot 500.

The plate lift unit 630 is mounted within the stage unit 200, and supplies the plates P loaded within the stage unit 200 one by one.

An operation of the clinical test apparatus will now be described.

The clinical test apparatus performs loading of reagents and samples, sample identification, scheduling of clinical tests, and dividing, transfer, incubation and measurement of samples and reagents.

Firstly, test tubes in which samples and reagents are contained are loaded on the loading unit 230. The mobile robot 500 is initialized at the docking unit 400. The samples are identified by a RFID system. A user inputs scheduling with respect to a clinical test of each sample.

If the clinical test begins, the mobile robot 500 moves to the reference robot 620 of the transfer unit 600, and then waits for at a standby position by the reference robot 620. The transfer robot 610 distributes the samples and the reagents into the plate P supplied from the plate lift unit 630. The transfer robot 610 seats the plate P in the mobile robot 500.

The mobile robot 500 transfers the plate P to the test station 300. The detector 525 mounted in the diagnostic module 520 of the mobile robot 500 calculates clinical test results within the test station 300.

After the clinical test is finished, the mobile robot 500 returns to the docking unit 400, takes an original position, and begins charging.

Since a clinical test is performed through a diagnostic module integrated with a mobile robot, a test process can be shortened. Further, since a plurality of clinical tests can be performed through a plurality of mobile robots, a parallel test is possible.

Although a mobile robot malfunctions during a clinical test, it can be easily replaced with another mobile robot. Thus, the yield of an overall system is not affected.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims. Therefore, all changes and modifications that fall within the metes and bounds of the claims, or equivalence of such metes and bounds are intended to be embraced by the appended claims.

The invention claimed is:

1. A clinical test apparatus comprising:
   a stage unit;
   a test station provided in the stage unit for performing a clinical test;
   a plurality of landmarks disposed on the top surface of the stage unit, each of the plurality of landmarks including four magnets disposed in a square shape to define a reference x-y coordinate, an origin of the reference x-y coordinate being a target position;
   a mobile robot comprising a diagnostic module in which a plate having samples and reagents loaded thereon is seated and a mobile module for transferring the diagnostic module to the test station; and
   a docking unit comprising a reference gripper fixed on the stage unit and a movement gripper for gripping the mobile robot with the reference gripper to dock the mobile robot at a reference position when the mobile robot is located between the reference gripper and the movement gripper,
   wherein the mobile module comprises:
      a base for moving on a top surface of the stage unit;
      a plurality of wheels for driving the base on the stage unit;
      four hall sensors disposed at the bottom of the base in a square shape to define a robot x-y coordinate, an origin of the robot x-y coordinate being a center position of the mobile robot, each hall sensor detecting a magnetic field of each magnet in each landmark to acquire an offset between a position of each hall sensor and x-axis or y-axis of the reference x-y coordinate; and
      a processor configured to initialize a position of the mobile robot with the reference position when the mobile robot is docked in the docking unit and determine a positional error (x, y) and a rotational error θ of the mobile robot based on offsets between positions of the four hall sensor and x-axis or y-axis of the reference x-y coordinate.

2. The clinical test apparatus of claim 1, wherein the mobile module further comprises a battery for providing power to the plurality of wheels and a charging connector for charging the battery, and the docking unit further comprises a charging terminal disposed at the movement gripper for contacting the charging connector when the mobile robot is docked in the docking units.

3. A mobile robot, comprising:

a diagnostic module in which a plate having samples and reagents loaded thereon is seated; and a mobile module having the diagnostic module mounted therein for transferring the diagnostic module to a test station where a clinical test is performed, wherein the mobile module comprises:

a base for moving on a top surface of a stage unit;

a plurality of wheels for driving the base on the stage unit;

four hall sensors disposed at the bottom of the base in a square shape to define a robot x-y coordinate, an origin of the robot x-y coordinate being a center position of the mobile robot, each hall sensor detecting a magnetic field of each magnet in each of a plurality of landmarks to acquire an offset between a position of each hall sensor and x-axis or y-axis of a reference x-y coordinate, the plurality of landmarks disposed on the top surface of the stage unit, each of the plurality of landmarks including four magnets disposed in a square shape to define the reference x-y coordinate; and a processor configured to initialize a position of the mobile robot with a reference position when the mobile robot is docked in a docking unit and determine a positional error (x, y) and a rotational error θ of the mobile robot based on offsets between positions of the four hall sensor and x-axis or y-axis of the reference x-y coordinate.

4. The mobile robot of claim 3, wherein the diagnostic module comprises a RFID reader for reading a RFID tag mounted in the plate.

5. The mobile robot of claim 3, wherein the diagnostic module comprises a detector for calculating results of the clinical test.

6. The mobile robot of claim 5, wherein the detector comprises a spectrophotometer.

7. The clinical test apparatus of claim 1, wherein the positional error (x, y) of the mobile robot is acquire by $$x = \frac{a-b}{2} + b, \; y = \frac{c-d}{2} + d,$$

where a and b denote offsets between positions of two hall sensors and x-axis of the reference x-y coordinate, and c and d denotes offsets between positions of remaining two hall sensors and y-axis of the reference x-y coordinate.

8. The clinical test apparatus of claim 7, wherein the rotational error θ of the mobile robot is acquire by $$\theta = \arcsin\left(\frac{|a-b|}{2 l_1}\right) \text{ or } \theta = \arcsin\left(\frac{|c-d|}{2 l_2}\right), 2 l_1$$

denotes a distance between two hall sensors corresponding to offsets a and b, and $2 l_2$ denotes a distance between two hall sensors corresponding to offsets c and d.

9. The mobile robot of claim 3, wherein the positional error (x, y) of the mobile robot is acquire by $$x = \frac{a-b}{2} + b, \; y = \frac{c-d}{2} + d,$$

where a and b denote offsets between positions of two hall sensors and x-axis of the reference x-y coordinate, and c and d denotes offsets between positions of remaining two hall sensors and y-axis of the reference x-y coordinate.

10. The mobile robot of claim 9, wherein the rotational error θ of the mobile robot is acquire by $$\theta = \arcsin\left(\frac{|a-b|}{2 l_1}\right) \text{ or } \theta = \arcsin\left(\frac{|c-d|}{2 l_2}\right), 2 l_1$$

denotes a distance between two hall sensors corresponding to offsets a and b, and $2 l_2$ denotes a distance between two hall sensors corresponding to offsets c and d.

* * * * *